United States Patent [19]
Schmutzler et al.

[11] Patent Number: 5,886,053
[45] Date of Patent: Mar. 23, 1999

[54] USE OF CAROTENOIDS FOR PRODUCING DRUGS FOR THE TREATMENT OF DERMATOSES

[75] Inventors: Wolfgang Schmutzler, Aachen; Karl Kolter, Limburgerhof, both of Germany

[73] Assignee: BASF Aktiengesellschaft, Ludwigshafen, Germany

[21] Appl. No.: 875,622

[22] PCT Filed: Feb. 2, 1996

[86] PCT No.: PCT/EP96/00381

§ 371 Date: Jul. 30, 1997

§ 102(e) Date: Jul. 30, 1997

[87] PCT Pub. No.: WO96/23489

PCT Pub. Date: Aug. 8, 1996

[30] Foreign Application Priority Data

Feb. 3, 1995 [DE] Germany ........................ 195 03 604.2
Oct. 25, 1995 [DE] Germany ........................ 195 39 743.6

[51] Int. Cl.$^6$ .................................................. A61K 31/015
[52] U.S. Cl. .......................... 514/763; 514/763; 514/861; 514/863; 514/864; 514/865; 514/870; 514/871; 514/886; 514/887; 424/401
[58] Field of Search ................................ 424/401, 78.02, 424/78.05; 514/763, 863, 861, 870, 871, 886, 887, 864, 865; 585/315

[56] References Cited

U.S. PATENT DOCUMENTS 5,034,228  7/1991  Maybeck et al. ........................ 424/401
5,453,447  9/1995  End et al. ............................... 424/450

FOREIGN PATENT DOCUMENTS 542 632  5/1993  European Pat. Off. .

OTHER PUBLICATIONS

Bolsmann et al., *Inflamm. Res.*, vol. 45 (Supp. 1), 1996, pp. S5–S6.
TM Florence, *Aust. N. Z. J. Ophthalmol.*, Feb. 1995, vol. 23, No. 1, pp. 3–7.
Franceschini et al., *Nouv. Presse Med.*, 1981, vol. 10, No. 23 (1938).
Oberlin et al., *Ann. Dermatol. Venereol.*, 1991, vol. 118, No. 11, pp. 824–825.
Lawlor et al., *Z. Hautkr.*, 1990, vol. 65, No. 1, pp. 17–27.
Scheurlein et al., *Gastroenterology*, vol. 106 (4 Supp.), 1994, A768.
Gonzalez–Huix et al., $9^{th}$ *Cong. of the European Soc. of Parenteral and Enteral Nutrition*, Barcelona, Spain, Sep. 13–16, 1987, Clin. Nutr. (EDINB), 6 (Spec. Supp.), 1987, p. 70.
Abad–Lacruz et al., $9^{th}$ *Cong. of the European Soc. of Parenteral and Enteral Nutrition*, Barcelona, Spain, Sep. 13–16, 1987, Clin. Nutr. (EDINB), 6 (Spec. Supp.), 1987, p. 36.
Zwadlo–Klarwasser et al., *Agent Actions 41, Spec. Conf. Issue: C99–C100*, 1994.
Forth et al., *Pharm. und Toxik.*, pp. 404–405, 4 Auflage.
Eichelberg et al., *Arch. Dermatol. Res.*, vol. 280, pp. 155–157, 1988.
Hollander et al., "Neues aus der amerikanischen Dermatologie", Der Hautarzt, pp. 379–383, 1971.
A. Taaffe, *Postgrad. Med. J.*, Dec. 1977, vol. 53, pp. 732–736.

Primary Examiner—Thurman K. Page
Assistant Examiner—Lakshmi Channavajjala
Attorney, Agent, or Firm—Keil & Weinkauf

[57] ABSTRACT

The use of carotenoids for producing drugs for the treatment of inflammatory disorders not caused by the action of light or an infection with microorganisms.

4 Claims, No Drawings

USE OF CAROTENOIDS FOR PRODUCING DRUGS FOR THE TREATMENT OF DERMATOSES

BACKGROUND OF THE INVENTION

1. Field of the Invention

This application is a 371 of PCT/EP96/00381 filed on Feb. 2, 1996. The present invention relates to the use of carotenoids for producing drugs for the treatment of inflammatory disorders not caused by an infection with microorganisms or by the action of light, in particular abacterial, non-photoinduced dermatoses.

Inflammatory disorders for the purpose of this invention may be either allergic or non-allergic in nature, but the inflammatory reaction of the affected tissue is not caused by an infection with microorganisms and is not induced by the action of light.

Examples of appropriate disorders are:

pollinosis (seasonal rhinitis)

perennial rhinitis polyposis nasi inflammatory disorders of the gastrointestinal tract such as regional enterocolitis (Crohn's disease), ulcerative colitis, irritable colon dermatoses, for example contact urticaria, urticaria pigmentosa allergic vasculitis insect allergy bronchial asthma allergic reactions of the outer eye allergic and pseudoallergic reactions to drugs systemic mastocytosis autoimmune disorders, for example systemic lupus erythematosus Sjögren's syndrome, thyreoditis, [sic], insulitis, glomerulonephritis.

Non-photoinduced, abacterial inflammatory dermatoses are in particular cutaneous vascular forms of allergy such as neurodermatitis or urticaria or else hyperkeratoses such as psoriasis.

It is highly probable that reactive oxygen species or singlet oxygen play an important part in the pathogenesis of various allergic and non-allergic inflammations. There is also suspected to be involvement of such species in degranulation with release of mediators from mast cells. It is certain that degranulation of mast cells and of basophilic granulocytes in blood represents the first step in the initiation of an allergic reaction.

One of the principal mediators of allergic reactions is histamine, and inhibition of its release or effect represents an important principle for the therapy of allergic inflammatory disorders.

2. Description of Related Art

Recent investigations have shown that histamine is released to considerable degrees not only in mast cells but also in human monocytes (G. Zwadlo-Klarwasser et al., Agent Actions 41, Special Conf. Issue: C99–C100, (1994)).

To date, glucocorticoids and $H_1$ antagonists for example have mainly been used for the treatment of allergic dermatoses disorders, the latter being suitable only for systemic use.

Used for the treatment of bronchial asthma are, besides bronchiospasmolytics, cromones or steroid therapeutic agents. Usually employed for autoimmune disorders are steroids or else immunosuppressants.

The use of retinol (vitamin A) and retinoic acid derivatives is known for the treatment of some inflammatory dermatoses. Thus, retinol has been used for the treatment of juvenile acne and of psoriasis, although the suitability of this therapy proved to be low because of the overdosage manifestations.

The retinoids isotretinoin and etretinate are also suitable in principle for the treatment of acne and inflammatory hyperkeratoses such as psoriasis, but, like retinol, they easily give rise to symptoms of overdosage. In addition, etretinate is to be categorized as very problematic because of its highly teratogenic effect.

(cf. "W. Forth (editor), Pharmakologie und Toxikologie, page 404–5, 4th Edition, BI Wissenschaftsverlag, Mannheim).

It has also been found that the retinoids isotretinoin and etretinate are able to inhibit histamine release in human mast cells (D. Eichelberg and W. Schmutzler, Arch. Dermatol. Res., 280, 155–157 (1988)). However, because of the side effects which have already been mentioned, these agents are not recommended unconditionally for therapeutic use.

It is furthermore known that carotenoids such as β-carotene (provitamin A) or canthaxanthin have been used for the treatment of light-induced dermatoses such as erythropoietic protoporphyria and urticaria solaris, and of dyschromias (vitiligo) (A. Hollander, "Neues aus der amerikanischen Dermatologie", Der Hautarzt, (1971) pp. 379–383). However, the therapeutic effect of carotenoids for urticaria solaris is regarded as uncertain (F. Lawlor et al., Z. Hautkrankh., 65, 17–27 (1989); A. Taaffe, Postgrad. Med. J., 53, 732–736 (1977).

To date there is no verified therapy for the treatment of allergic inflammatory neurodermatitis.

SUMMARY OF THE INVENTION

It is an object of the present invention to extend the possibilities for treatment of certain inflammatory disorders, especially dermatoses, by providing novel agents for this purpose.

We have found that this object is achieved by carotenoids which inhibit histamine release and are suitable for the use defined at the outset.

Carotenoids used according to the invention are, besides β-carotene which is preferred, also canthaxanthin, zeaxanthin, citranaxanthin, astaxanthin or lycopene. The carotenoids are preferably used in the form of solubilizates.

The carotenoids can be used both in topical and in systemically acting preparations.

Suitable in principle for topical use are all presentations customary for this purpose, such as ointments, creams, gels, lotions, emulsions or solutions.

For systemic treatment, the carotenoids can be either injected or administered orally. Suitable oral presentations are all the forms customary for this purpose, such as capsules, coated or uncoated tablets or liquid preparations.

The production of presentations of these types and the pharmaceutical ancillary substances customary for these purposes are known to the skilled worker.

DESCRIPTION OF THE PREFERRED EMBODIMENTS

Presentations for topical use can contain from 0.05 to 15, preferably 0.2 to 4, % by weight of carotenoids. The dosage may vary within wide limits depending on the severity of the disorder to be treated because, owing to the good tolerabilities of the carotenoids, side effects are virtually ruled out.

Daily doses of from 5 to 750, preferably 10 to 300, mg are recommended for systemic treatment.

Because of the good tolerability and low toxic potential of the carotenoids, these are outstandingly suitable for producing drugs for the treatment of acute or chronic recurrent inflammatory disorders which are not induced by light and not caused by an infection with microorganisms.

According to the invention carotenoids are suitable for producing drugs for the treatment of allergic inflammatory disorders of the nasal mucosa and of the intestinal mucosa. They are furthermore suitable for treating systemic allergic inflammatory disorders. The production of drugs for the treatment of cutaneous disorders not induced by the action of light is preferred.

Because of the inhibitory effect on histamine release, they are particularly preferably suitable for treating allergic inflammatory dermatoses such as neurodermatitis.

The histamine-inhibiting effect is described in the experiments below. The carotenoid used therein was β-carotene in the form of a solubilizate consisting of 4% by weight of β-carotene, 22% by weight of ethoxylated 12-hydroxystearic acid as solubilizer and water to 100% by weight.

The experiments were carried out on adenoidal mast cells, cutaneous mast cells and peripheral monocytes. Stimulation took place with concanavalin A or the mediator of inflammation C5a.

Determination of the histamine release from adenoidal mast cells, peripheral blood monocytes and cutaneous mast cells Test method
  1. Mast cells from adenoid vegetations
  The medium used throughout is complete Hanks buffer of pH 7.4 with the following composition:
  1. 100 ml of 8.5 g % NaCl
  2. 10 ml of 4.0 g % KCl
  3. 10 ml of 0.6 g % $KH_2PO_4$
  4. 10 ml of 0.6 g % $Na_2HPO_4 \times 2H_2O$
  5. 10 ml of 3.5 g % $NaHCO_3$ (always freshly prepared)
  6. 10 ml of 1.4 g % $CaCl_2 \times 2H_2O$
  7. 10 ml of 1.0 g % $MgCl_2 \times 6H_2O$
  8. 10 ml of 1.0 g % $MgSO_4 \times 7H_2O$
  9. 1.0 g of D-glucose
  10. Make up to 1000 ml with double-distilled water The cells were stimulated to release histamine with concanavalin A (Sigma, Munich). ps Isolation of the mast cells Adenoid vegetations (third tonsil) are placed in Hanks buffer immediately after the operation and subjected to the complete experiment within 90 to 120 minutes. For this purpose, the tissue is first comminuted with a McIlwain and Buddle tissue chopper (reference: Handbuch der experimentellen Pharmakologie, Volume 18/1, 342, 1966). One part by weight of adenoid is taken up in 5 times the volume of Hanks buffer and placed in an ice bath. A plastic syringe (without needle) is then used to aspirate the suspension and expel it again five times. After being left in an ice bath for 10 minutes, the same procedure is repeated again. The cell suspension is filtered through three layers of gauze and then centrifuged at 125×g for 5 minutes. The supernatant is aspirated off, the sediment is resuspended in 1 ml of Hanks buffer and the volume is made up with 10 ml of Hanks buffer. The cell suspension is filtered through a Vyon filter with a pore size of 100μ (W. Köpp Zellkautschuk, Aachen), centrifuged again, resuspended and again filtered through a Vyon filter. Centrifugation is then carried out again and the sediment is taken up in 1 ml of Hanks buffer. The cells in this suspension are counted after staining with Alcian blue solution (1 g of Alcian blue, 45 ml of absolute alcohol, 45 ml of 1% sodium sulfate hydrite, 10 ml of glacial acetic acid).

For the test, 2 to $3 \times 10^5$ mast cells were equilibrated with Hanks buffer and the various concentrations of beta-carotene in a water bath at 37° C. After 5 minutes, 50 mg of concanavalin A were added in a volume of 50 μl so that the final volume of the mixture was 500 μl. After incubation at 37° C. for a further 10 minutes, the mixture was centrifuged at 4° C., and the histamine was determined separately in the supernatant and sediment using a radioimmunoassay (Dianova-Immunotech Vertriebsgesellschaft, Hamburg).

The results are detailed in Table I.

TABLE I

| Con A-stimulated histamine release in adenoid cells | |
|---|---|
| Concentrations [mol/l] of β-carotene or placebo | Histamine release [% total histamine] average (n = 7) |
| | β-Carotene |
| 0 (buffer baseline) | 21.7 |
| $10^{-6}$ | 16.5 |
| $10^{-5}$ | 12.5 |
| $10^{-4}$ | 7.1 |
| $10^{-3}$ | 2.1 |
| | Placebo |
| 0 (buffer baseline) | 14.6 |
| $10^{-6}$ | 12.9 |
| $10^{-5}$ | 15.2 |
| $10^{-3}$ | 4.7 |

2. Monocytes

The monocytes are isolated with a purity of about 85% from leukocyte concentrates (buffy coats) by gradient centrifugation. For this purpose, the buffy coats are distributed to two tubes and brought to a total volume of 30 ml with spinner medium (Gibco, Paisley, Scotland). This suspension is cautiously overlaid on 20 ml of Ficoll (Pharmacia, Freiburg i. Brsg.) and centrifuged at 532×g and 20° C. for 40 minutes. The band above the Ficoll is removed (the remainder is discarded) and made up to 50 ml with spinner medium. After centrifugation at 299×g and 4° C. for 10 minutes, the sediment is resuspended in 10 ml of spinner medium and centrifuged once again. The sediment is resuspended in 3 ml and placed on a prepared 55% strength Percoll gradient (300 to 600 million mononuclear cells/tube). After centrifugation at 532×g and 20° C. for 40 minutes, the monocytes are located in the upper band, and the lymphocytes are located in the lower band. The upper band is removed and washed three times in spinner (resuspending the sediment in spinner), making up to 50 ml and centrifuging at 299×g for 10 minutes). After the second wash, the number of living monocytes is established by a vitality count with trypan blue, and after the last wash the cell count is adjusted to 3 million cells per 200 μl of Iscove's medium.

The sediment is then resuspended in such a way that 200 μl contain about $3 \times 10^6$ live cells.

Then 200 μl of Iscove's medium (Gibco, Paisley, Scotland) are added to the mixture, and 50 μl of a dilution of β-carotene or placebo solution in Iscove's medium in order to obtain the required final concentration. After equilibration for 60 minutes, either 50 μl of buffer or 50 μl of C5a solution (Sigma, Munich) are added to produce a final C5a concentration of $10^{-8}$ M for a final volume of 500 μl.

Incubation for 60 minutes is followed by centrifugation and determination of the histamine content in the supernatant and sediment separately using a radioimmunoassay (Dianova-Immunotech, Hamburg).

The results are detailed in Table II.

TABLE II

Spontaneous and C5a-induced histamine release (as % of the total histamine) from human peripheral blood monocytes in the presence and absence of β-carotene (n = 4)

| Conc. [mol/l] | β-Carotene | Placebo |
|---|---|---|
| | Spontaneous histamine release [%] | |
| 0 (baseline) | 4.1 | 4.1 |
| $10^{-6}$ | 1.9 | 1.6 |
| $10^{-5}$ | 0.7 | 1.8 |
| $10^{-4}$ | 1.7 | 3.2 |
| $10^{-3}$ | 5.7 | 21.3 |
| | C5a | |
| 0 (baseline) | 2.4 | 2.4 |
| $10^{-6}$ | 2.9 | 3.2 |
| $10^{-3}$ | 9.3 | 26.9 |

3. Enzymatic isolation of human cutaneous mast cells
DMEM buffer: Dulbecco's minimum essential medium The cutaneous mast cells are isolated from prepuce tissue which is placed in buffer immediately after the operation and further processed within 24 h. The tissue is manually comminuted and washed twice by suspending the tissue in 10 ml of DMEM buffer/1 g of tissue, centrifuging at 1000 rpm and 4° C. for 5 minutes and removing the buffer. It is subsequently treated with collagenase I (Washington/Cell Systems, Remagen; 142 U/mg) and hyaluronidase type I-S (Sigma; 440 U/mg), employing 10 ml of DMEM buffer with 1.5 mg/ml collagenase and 0.5 mg/ml hyaluronidase per gram of tissue. The mixture is incubated in a shaking bath at 37° C. for 60 minutes. After the incubation, a syringe is used to prepare by mechanical dispersion a suspension, which is filtered through three layers of gauze and then centrifuged at 1000 rpm and 4° C. for 5 minutes. The supernatant is decanted off, the cell pellet is suspended in 1 ml of DMEM buffer, and the volume is made up to 10 ml with buffer and the mixture is centrifuged once again under the abovementioned conditions. This procedure is repeated twice more, and the cell pellet is taken up in 1 ml of DMEM buffer.

Cell counting is then carried out, staining the cells with toluidine blue by the Kimura method (450 µl of Kimura solution per 50 µl of cell suspension). Counting is carried out in a Neubauer chamber including all 9 large squares.

For the test, the cell pellets were equilibrated with, in each case, 2 ml of a $CaCl_2$-containing DMEM buffer (2.8 mmolar in $CaCl_2$) and the various concentrations of beta-carotene in a water bath at 37° C. After 5 minutes, 50 mg of substance P (neuropeptide; supplied by Sigma) were added in a volume of 50 µl so that the final volume was 500 µl. After incubation at 37° C. for a further 10 minutes, the mixture was centrifuged at 4° C., and the histamine was determined separately in the supernatant and sediment using a radioimmunoassay (Dianova-Immumotech Vertriebsgesellschaft, Hamburg).

The results are detailed in Table III.

TABLE III

Substance P-stimulated histamine release in cutaneous mast cells

| Concentration [mol/l] | Histamine release[+) [% total histamine] |
|---|---|
| β-Carotene | |
| 0 | 9.1 |
| $10^{-5}$ | 8.2 |
| $10^{-4}$ | 4.5 |
| $10^{-3}$ | 5.4 |
| Placebo | |
| 0 | 5.2 |
| $10^{-5}$ | 6.2 |
| $10^{-3}$ | 6.2 |

[+)average for n = 11 experiments

Inhibition of histamine release occurs with increasing β-carotene concentration. This is not observed in the blank experiments (placebo).

We claim:

1. A process for treating abacterial and non-photoinduced neurodermatitis in a patient in need thereof which comprises administrating to said patient a pharmaceutical composition containing an effective amount of a carotenoid.

2. A process for treating non-photoinduced urticaria in a patient in need thereof which comprises administrating to said patient a pharmaceutical composition containing an effective amount of a carotenoid.

3. A process as defined in claim 1, wherein the carotenoid is β-carotene.

4. A process as defined in claim 2, wherein the carotenoid is β-carotene.

* * * * *